US011439343B1

(12) United States Patent
Tan et al.

(10) Patent No.: US 11,439,343 B1
(45) Date of Patent: Sep. 13, 2022

(54) NON-CONTACT IDENTIFICATION OF SLEEP AND WAKE PERIODS FOR ELDERLY CARE

(71) Applicant: Tellus You Care, Inc., San Francisco, CA (US)

(72) Inventors: Huiyuan Tan, Sunnyvale, CA (US); Kevin Hsu, San Francisco, CA (US); Tania Abedian Coke, San Francisco, CA (US)

(73) Assignee: Tellus You Care, Inc., San Francisco, CA (US)

(*) Notice: Subject to any disclaimer, the term of this patent is extended or adjusted under 35 U.S.C. 154(b) by 313 days.

(21) Appl. No.: 16/856,116

(22) Filed: Apr. 23, 2020

Related U.S. Application Data

(60) Provisional application No. 62/849,191, filed on May 17, 2019.

(51) Int. Cl.
*A61B 5/00* (2006.01)
*A61B 5/15* (2006.01)
*A61B 5/11* (2006.01)

(52) U.S. Cl.
CPC .......... *A61B 5/4809* (2013.01); *A61B 5/1115* (2013.01); *A61B 5/150809* (2013.01); *A61B 5/7267* (2013.01)

(58) Field of Classification Search
CPC ................ A61B 5/4809; A61B 5/1115; A61B 5/150809; A61B 5/7267
USPC ........................................................ 600/595
See application file for complete search history.

(56) References Cited

U.S. PATENT DOCUMENTS

| 2011/0144517 A1* | 6/2011 | Cervantes | A61B 5/08 600/538 |
| 2013/0053653 A1* | 2/2013 | Cuddihy | A61B 5/0816 600/301 |
| 2013/0156297 A1* | 6/2013 | Shotton | G06K 9/6282 382/159 |
| 2015/0141762 A1* | 5/2015 | Heinrich | A61B 7/003 600/301 |
| 2016/0144174 A1* | 5/2016 | Ferree | A61B 5/4815 600/595 |

(Continued)

FOREIGN PATENT DOCUMENTS

WO WO 2015/195958 A1 12/2015

*Primary Examiner* — Kerri L McNally
(74) *Attorney, Agent, or Firm* — Muirhead and Saturnelli, LLC

(57) ABSTRACT

Determining sleep patterns of a user includes detecting a plurality of point clouds, each corresponding to a different position of the user at different times, forming a plurality of bounding boxes, each corresponding to coordinates of captured points of one of the point clouds, creating a wake/sleep classifier based on features of the point clouds, determining sleep positions of the user as a function of time based on the bounding boxes, and determining sleep patterns of the user based on the sleep positions of the user and on results of the sleep/wake classifier. Detecting a plurality of point clouds may include using a tracking device to capture movements of the user. The features of the point clouds may include intermediate data that is determined using scalar velocities of points in the point clouds, absolute velocities of points in the point clouds, and/or counts of points in the point clouds.

22 Claims, 8 Drawing Sheets

(56) References Cited

U.S. PATENT DOCUMENTS

2017/0224256 A1* 8/2017 Kirenko ............... A61B 5/7485
2019/0108740 A1* 4/2019 Coke ...................... H04L 67/22

* cited by examiner

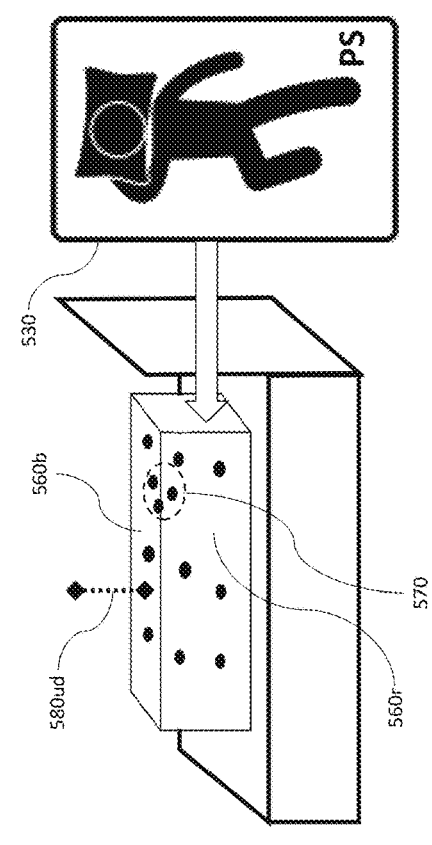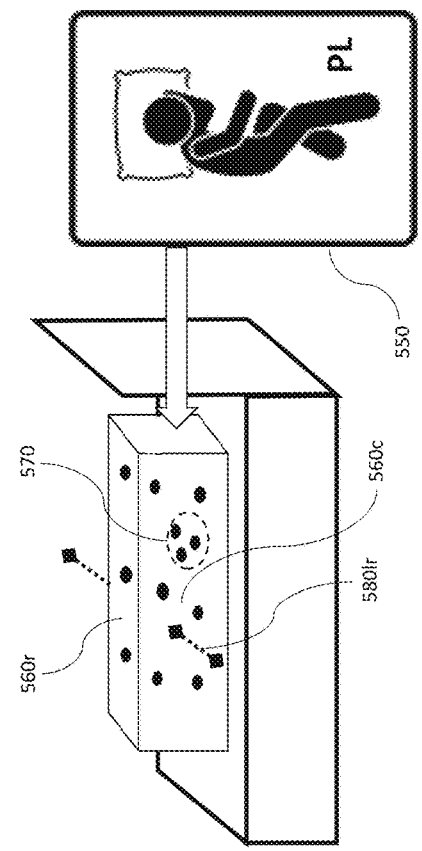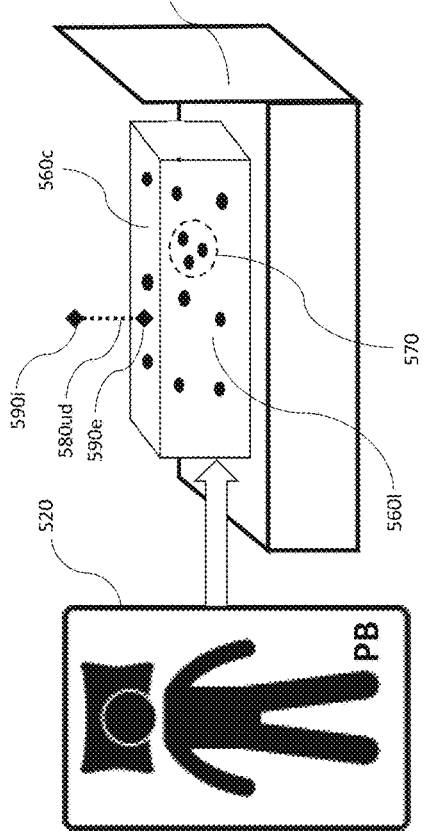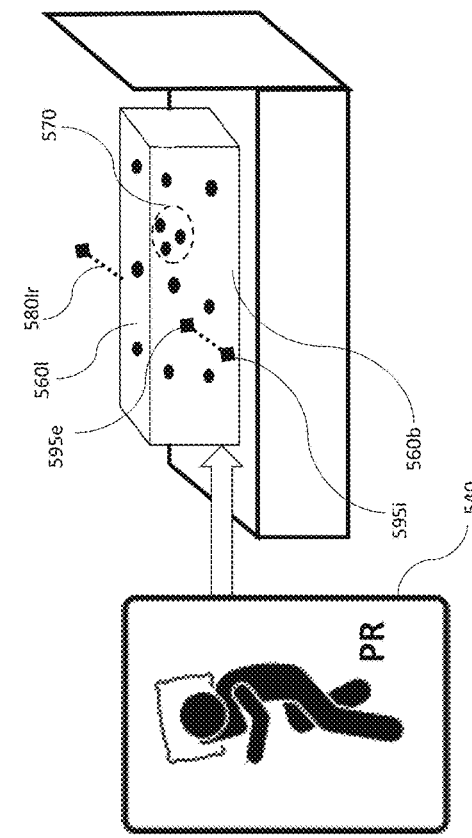

NON-CONTACT IDENTIFICATION OF SLEEP AND WAKE PERIODS FOR ELDERLY CARE

CROSS-REFERENCE TO RELATED APPLICATIONS

This application claims priority to U.S. Prov. App. No. 62/849,191, filed on May 17, 2019, and entitled "NON-CONTACT IDENTIFICATION OF SLEEP AND WAKE PERIODS FOR ELDERLY CARE", which is incorporated herein by reference.

TECHNICAL FIELD

This application is directed to the field of remote monitoring of sleep information and patterns using interconnected hardware and software, and machine learning, and more particularly to remote monitoring of sleep and wake periods, body positions during sleep and turning patterns of elderly people using an ultra-wideband radar and machine learning.

BACKGROUND OF THE INVENTION

Healthy sleep is a fundamental human need and a key factor of wellness. Recent decades have seen an increase in various sleep disorders. Thus, according to epidemiological studies, over half of older adults suffer from insomnia, often untreated, while 44% of older persons experience one or more of the nighttime symptoms of insomnia at least a few nights per week.

A significant percent of population, up to 10% of men and 4% of women between the ages of 30 and 49 years, and up to 17% of men and 9% of women between the ages of 50 and 70, suffer from an obstructive sleep apnea (much higher numbers than in earlier research). New data show a significant underreporting of subjective complaints of sleepiness in all age categories, which leaves a significant number of apnea cases undiagnosed and untreated. Similar problems exist in other sleep disorder categories, such as hypersomnias, parasomnias, sleep-related moving disorders and disorders of the sleep-wake rhythm.

Fast development of sleep medicine is looking to address growing challenges to the public health stemming from sleep disorders. The numbers of sleep experts and physicians is growing and emergence of sleep centers, a new type of inpatient healthcare facilities for professional assessment of sleep disorders, is becoming a core of sleep diagnostics.

An important direction in research, diagnostics and treatment of sleep disorders, is age-related and aimed at seniors. Sleeping patterns and mechanisms are noticeably changing with age. According to new studies, the total sleep time (TST) is decreasing by an average 27 minutes per night through every subsequent decade-based age group, starting with the 40-50 year range. Shrinking sleep time for the elderly is caused by a variety of factors, including more frequent awakenings and night time out of bed. In a recent study, average numbers of both the EEG (electroencephalogram tracked) arousals and the awakenings per night have been over 20% higher for participants in the 50-70 age group compared with the 40-50 year group. The overall sleep efficiency is also significantly higher for younger age groups. One indicator of sleep problems is a persistent tossing and turning in bed for prolonged periods of night time when an individual is unable to find a convenient sleeping position.

It is established that certain types of sleep deficiencies among seniors are strongly contributing to the onset of dementia and other serious illnesses. Accordingly, sleep medicine research and studies, combined with the worldwide statistics of aging population, emphasize the need in new mass market solutions for collecting and processing sleep information for seniors located at care facilities and homes. While sleep centers, supplied with high-end, complex and invasive equipment for polysomnography, represent a standard in sleep disorder diagnostics, they are designated for short-term inpatient studies and cannot address early everyday tracking of sleep information for hundreds of millions of seniors.

Multiple mobile, stationary and semi-stationary devices and related software applications have been proposed for collecting and analyzing sleep data, including regular smartphones with motion sensors, smart watches (Nokia Steel, Polar M430), other wearable devices (Fitbit Versa bracelet, Oura ring), bed pads and similar sleep monitors (Withings Sleep, Beddit 3, Emfit QS), Radar Health Monitor developed by Kyoto University and Panasonic and many more. Notwithstanding a significant progress in the area, most of currently marketed solutions are intrusive, some of them require permanent maintenance, and many lack accuracy in sleep tracking.

Accordingly, it is useful to develop new mechanisms for reliable tracking of sleep information and patterns, including sleep and wake periods, sleeping positions, changes of sleep positions, and turning in bed.

SUMMARY OF THE INVENTION

According to the system described herein, determining sleep patterns of a user includes detecting a plurality of point clouds, each corresponding to a different position of the user at different times, forming a plurality of bounding boxes, each corresponding to coordinates of captured points of one of the point clouds, creating a wake/sleep classifier based on features of the point clouds, determining sleep positions of the user as a function of time based on the bounding boxes, and determining sleep patterns of the user based on the sleep positions of the user and on results of the sleep/wake classifier. Detecting a plurality of point clouds may include using a tracking device to capture movements of the user. The tracking device may use radar. The features of the point clouds may include intermediate data that is determined using scalar velocities of points in the point clouds, absolute velocities of points in the point clouds, and/or counts of points in the point clouds. At least some of the features may be filtered according to distance from a tracking device that is used to detect the plurality of point clouds. The intermediate data may include a bag of point counts corresponding to a set of point counts at a series of sequential time frames, a bag of velocities corresponding to a set of point velocities at a series of sequential time frames, and/or a bag of absolute velocities corresponding to a set of absolute velocities at a series of sequential time frames. A set of aggregating, scaling and filtering functions may be applied to the intermediate data to provide short-term feature aggregation values and mid-term feature aggregation values. The short-term feature aggregation values may be determined based on time slots corresponding to a relatively low number of sequential time frames. The feature aggregation values may include mean values, median values, sum of values, minimum values and maximum values, and/or scaling function include logarithmic scaling function values. The mid-term feature aggregation values may be derived from the short-term feature aggregation values. The mid-term feature aggregation values may be determined based on epochs that represent contiguous collections of time slots. The features of the point clouds may be used with truth information as training data for machine learning to provide an assessment of relative feature importance. The assessment of relative feature importance may be determined using random forest machine learning. Determining sleep positions may include determining if a breathing direction of the user is vertical or horizontal. If the breathing direction is vertical, the sleep position may be determined to be that the user is lying on the back of the user in response to a heart area of the user being detected on a left side of the user and the sleep position may be determined to be that the user is lying on the stomach of the user in response to the heart area of the user being detected on a right side of the user. If the breathing direction is horizontal, the sleep position may be determined to be that the user is lying on a left of the user in response to a heart area of the user being detected in a relatively lower disposition and the sleep position may be determined to be that the user is lying on a right side of the user in response to the heart area of the user being detected in a relatively upper disposition. Sleep patterns of the user may be determined based on correspondence of the sleep positions of the user with the results of the sleep/wake classifier as a function of time. Determining sleep patterns of a user may also include tracking daily sleep patterns for the user. Determining sleep patterns of a user may also include detecting a significant deviation from the daily sleep patterns. Determining sleep patterns of a user may also include providing an alarm in response to detecting the significant deviation from the daily sleep patterns.

According further to the system described herein, a non-transitory computer readable medium contains software that determines sleep patterns of a user. The software includes executable code that detects a plurality of point clouds, each corresponding to a different position of the user at different times, executable code that forms a plurality of bounding boxes, each corresponding to coordinates of captured points of one of the point clouds, executable code that creates a wake/sleep classifier based on features of the point clouds, executable code that determines sleep positions of the user as a function of time based on the bounding boxes, and executable code that determines sleep patterns of the user based on the sleep positions of the user and on results of the sleep/wake classifier. Detecting a plurality of point clouds may include using a tracking device to capture movements of the user. The tracking device may use radar. The features of the point clouds may include intermediate data that is determined using scalar velocities of points in the point clouds, absolute velocities of points in the point clouds, and/or counts of points in the point clouds. At least some of the features may be filtered according to distance from a tracking device that is used to detect the plurality of point clouds. The intermediate data may include a bag of point counts corresponding to a set of point counts at a series of sequential time frames, a bag of velocities corresponding to a set of point velocities at a series of sequential time frames, and/or a bag of absolute velocities corresponding to a set of absolute velocities at a series of sequential time frames. A set of aggregating, scaling and filtering functions may be applied to the intermediate data to provide short-term feature aggregation values and mid-term feature aggregation values. The short-term feature aggregation values may be determined based on time slots corresponding to a relatively low number of sequential time frames. The feature aggregation values may include mean values, median values, sum of values, minimum values and maximum values, and/or scaling function include logarithmic scaling function values. The mid-term feature aggregation values may be derived from the short-term feature aggregation values. The mid-term feature aggregation values may be determined based on epochs that represent contiguous collections of time slots. The features of the point clouds may be used with truth information as training data for machine learning to provide an assessment of relative feature importance. The assessment of relative feature importance may be determined using random forest machine learning. Determining sleep positions may include determining if a breathing direction of the user is vertical or horizontal. If the breathing direction is vertical, the sleep position may be determined to be that the user is lying on the back of the user in response to a heart area of the user being detected on a left side of the user and the sleep position may be determined to be that the user is lying on the stomach of the user in response to the heart area of the user being detected on a right side of the user. If the breathing direction is horizontal, the sleep position may be determined to be that the user is lying on a left of the user in response to a heart area of the user being detected in a relatively lower disposition and the sleep position may be determined to be that the user is lying on a right side of the user in response to the heart area of the user being detected in a relatively upper disposition. Sleep patterns of the user may be determined based on correspondence of the sleep positions of the user with the results of the sleep/wake classifier as a function of time. The software may also include executable code that tracks daily sleep patterns for the user. The software may also include executable code that detects a significant deviation from the daily sleep patterns. The software may also include executable code that provides an alarm in response to detecting the significant deviation from the daily sleep patterns.

The proposed system offers non-contact identification of sleep and wake periods, sleeping positions and patterns of turning in bed based on classifiers acquired through machine learning and other algorithms and utilizing velocity, coordinate and directional data collected from point clouds, obtained by an always-on tracking device, embedded into a room or other facility where a user resides; the device may include one or several ultra-wideband radars, a chipset, a wireless connection and possibly other components.

Various aspects of system functioning are explained as follows:

1. A tracking device may constantly capture high precision data from moving objects in a room where a user resides. Movements may include user walking, standing, sitting, lying down on a bed or a floor, etc.; movements with a smaller amplitude may include breathing and heartbeat.
2. Captured data may be presented in the form of point clouds, showing coordinates of moving points; information on radial velocity may also be available for each captured point.
3. A bounding box of a point cloud is a smallest cuboid in standard coordinates that encloses the point cloud; a disposition and relative lengths of dimensions of the bounding box may help identify user state—for example, discriminate between walking (or standing) and lying down.
4. Point clouds may be processed by the system in many different ways: to identify user movement state and position, to track user behavior and presence in the room, to collect vital signs, such as breathing, heart rate, etc.

In order to design a set of features for machine learning to produce a classifier of sleep/wake states, the system may use aggregated velocity information for the point clouds captured over several periods of time, where multiple ways of time grouping are employed. Initially, point clouds may be collected by the tracking device frame-by-frame with a frame frequency, for example, of four frames per second. Such frame-by-frame point clouds may be unstable even for a relatively static user lying in the bed; therefore, direct usage of the frame-by-frame point clouds for machine learning may not be efficient. Instead, the system may use several levels of grouping time intervals:

(i) Time slots—relatively short intervals spanning several adjacent frames; for example, a one-second time slot with four frames.
(ii) Ordinary epochs—uniform, relatively long (compared with a single slot) time intervals spanning several adjacent slots and running from a start of a data collection session, such as one-minute intervals with 60 adjacent time slots per interval. Each slot occupies a certain position within an ordinary epoch containing the time slot.
(iii) Centered epochs have the same length as ordinary epochs but are differently positioned
centered epochs are centered around a chosen slot to provide an analog of sliding feature aggregation (such as a sliding average or a sliding maximum).

The system may use three types of raw data associated with point clouds for aggregation over time periods (i)-(iii):
(a) Scalar velocities for each point—positive or negative numbers, depending on the directions relative to the radar front.
(b) Absolute velocities (directions are ignored).
(c) Point counts in each point cloud.

The intermediate data used for aggregation combine each type of the raw data for a given time slot $\tau=\{t_1, \ldots t_n\}$ (where the slot includes $\eta$ frames $t_i$) as follows:

A. A bag of point counts $\mathcal{N}_{\tau_\tau}=\{m_1, \ldots m_n\}$, where $m_i$ is a point count for the point cloud captured for the frame $t_i$.

B. A bag of velocities $\mathcal{V}_{\tau_\tau}=\{v_1^1, v_1^{m_1}, \ldots v_n^1, \ldots v_n^{m_n}\}$ is the set of all point velocities in the frames forming the slot $\tau$.

C. A bag of absolute velocities $\mathcal{V}_{\tau_\tau}^+$—same as previous, where each velocity is represented by its absolute value.

Prior to building the intermediate data, point clouds captured for each frame may be pre-processed, including elimination of systemic noise and normalization.

Training features are produced from the intermediate data $\mathcal{V}_{\tau_\tau}, \mathcal{V}_{\tau_\tau}^+, \mathcal{N}_{\tau_\tau}$ using the following aggregation and scaling process:

I. A set of aggregating, scaling and filtering functions  is chosen; examples of aggregation may include mean, median, sum or minimum/maximum values of the intermediate data; examples of scaling may include a logarithmic function or a distance adjusting coefficient based on a distance between a user and a tracking device; point filtering may also include a distance based approach.

II. A short-term feature aggregation $\mathcal{V}_{\tau_\tau}, \mathcal{V}_{\tau_\tau}^+,$  $\mathcal{N}_{\tau_\tau} \to \{\mathcal{F}_{\tau_\tau}\}$ yields slot-based training features $\mathcal{F}_{\tau_\tau}$ associated with each slot T and derived from a certain intermediate data component $\mathcal{V}_{\tau_\tau}, \mathcal{V}_{\tau_\tau}^+,$ $\mathcal{N}_{\tau_\tau}$ via a specific aggregation and scaling function .

III. A mid-term feature aggregation $\{\mathcal{F}_{\tau_\tau}\} \to \{\mathcal{F}_{\tau_\varepsilon}\}$, $\{\mathcal{F}_{\tau_{\varepsilon_c}}\}$ yields epoch-based training features $\mathcal{F}_{\tau_\varepsilon}$ (for ordinary epochs) and $\mathcal{F}_{\tau_{\varepsilon_c}}$ (for centered epochs), each derived from a certain slot-based feature $\mathcal{F}_{\tau_\tau}$ using a specific aggregation and scaling function to integrate slot-based features within an ordinary or centered epoch.

Examples of eighteen short-term and mid-term features used for machine learning and yielding a high-quality sleep/wake classifier is presented in Tables 1 and 2, below. Table 1 shows six short-term, slot-based features $\mathcal{F}_{\tau_\tau}^1, \ldots \mathcal{F}_{\tau_\tau}^6$ with aggregating functions including mean and median values and a (partially used) logarithmic scaling function. Table 2 shows twelve mid-term, epoch-based features $\mathcal{F}_{\tau_\varepsilon}^1, \ldots \mathcal{F}_{\tau_\varepsilon}^6, \mathcal{F}_{\tau_{\varepsilon_c}}^1, \ldots \mathcal{F}_{\tau_{\varepsilon_c}}^6$, where the first six features have been derived from short-term features for ordinary epochs and the next six have been derived from centered epochs. Aggregation functions in Table 2 represent sum and maximum values, and an additional filtration of cloud points by a distance of the point clouds from the tracking device is applied in several cases.

Machine learning for building a reliable classifier for sleep/wake identification may be conducted using many different methods and algorithms. Truth information on the sleep/wake state of users within the training data set may be obtained using EEG technique or other invasive or non-invasive mechanisms, including, with user's permission, direct observations by assisting personnel. A category of machine learning methods, such as the random forest method, may provide an assessment of relative feature importance for the resulting classifier. Table 3 includes an example of weighted feature ranking for top ten features of the eighteen-feature set explained above.

TABLE 1

| | Short-term feature aggregation | | | |
|---|---|---|---|---|
| | Aggregating function | | Scaling | |
| Raw data | mean | median | function | Notation |
| $V_\tau$ | + | | | $F_\tau^1$ |
| $V_\tau$ | | + | | $F_\tau^2$ |
| $N_\tau$ | + | | log | $F_\tau^3$ |
| $N_\tau$ | | + | log | $F_\tau^4$ |
| $V_\tau^+$ | + | | | $F_\tau^5$ |
| $V_\tau^+$ | | + | | $F_\tau^6$ |

TABLE 2

Mid-term feature aggregation

| Entry feature | Aggregating function | | | Adjusted by | Notation by epoch | |
|---|---|---|---|---|---|---|
| | sum | maximum | distance | | ordinary | centered |
| $F^5_\tau$ | + | | | | $F^1_\varepsilon$ | $F^1_{\varepsilon_c}$ |
| $F^6_\tau$ | + | | | | $F^2_\varepsilon$ | $F^2_{\varepsilon_c}$ |
| $F^5_\tau$ | | + | | | $F^3_\varepsilon$ | $F^3_{\varepsilon_c}$ |
| $F^6_\tau$ | | + | | | $F^4_\varepsilon$ | $F^4_{\varepsilon_c}$ |
| $F^5_\tau$ | | | + | + | $F^5_\varepsilon$ | $F^5_{\varepsilon_c}$ |
| $F^6_\tau$ | | | + | + | $F^6_\varepsilon$ | $F^6_{\varepsilon_c}$ |

TABLE 3

Feature ranking

| Feature | Importance |
|---|---|
| $F^1_\varepsilon$ | 100 |
| $F^2_\varepsilon$ | 68 |
| $F^1_{\varepsilon_c}$ | 56 |
| $F^2_{\varepsilon_c}$ | 48 |
| $F^5_{\varepsilon_c}$ | 43 |
| $F^6_\varepsilon$ | 40 |
| $F^5_\varepsilon$ | 40 |
| $F^3_{\varepsilon_c}$ | 37 |
| $F^6_{\varepsilon_c}$ | 29 |
| $F^3_{\varepsilon_c}$ | 29 |

In order to detect sleeping positions and turning patterns of a user, the system may use tracking data on coordinates and directions utilized for measuring vital signs, such as breathing and heart rates. Specifically, breathing direction (up-and-down or left-and-right) during a time interval, combined with the approximate coordinates of a heart area of the user (where heartbeat rates are measured based on tracking data), may be instrumental for detecting the current sleeping position, which may be estimated as follows:

- lithe breathing direction for a user lying in the bed is vertical, up-and-down, it is likely that the user is lying on the back or the stomach. Since the heart area for most users is shifted to the left within a user's body, it is likely that if, in addition to user's up-and-down breathing direction, heartbeats occur on the left side of bounding boxes of point clouds, then the user is sleeping on the back.
- Conversely, if the breathing direction is still vertical but the heartbeat area is shifted to the right side of bounding boxes, the user is probably sleeping on the stomach.
- Similarly, the system may analyze a situation with a horizontal, left-and-right breathing direction, which corresponds to the user sleeping on the left or right side. In this case, an asymmetry in disposition of the heart area may help identify on which side the user is lying: an upper disposition of the heart area speaks in favor of sleeping on the right side, while a lower disposition correlates with sleep on the left side.

The system may track subsequent periods of time when a user stays in a permanent sleeping position and derive sleeping position patterns for the user. Simultaneously, the system may detect changes in the sleeping position, which correspond to turning in bed. The patterns may be reflected in user sleep analytics and may be continuously compared with dynamic user sleep behavior. Such analytics and comparisons carry important information about sleep quality and potential sleep disorders. For example, long periods of time (exceeding age norms) when a user is frequently turning in bed without sleeping, which is detected via the sleep/wake classification, as explained elsewhere herein, may lead to an alarm and a suggestion by the system to conduct a comprehensive study of the user in a sleep center.

BRIEF DESCRIPTION OF THE DRAWINGS

Embodiments of the system described herein will now be explained in more detail in accordance with the figures of the drawings, which are briefly described as follows.

FIGS. 5A-5D are schematic illustrations of identifying sleeping positions of a user, according to an embodiment of the system described herein.

DETAILED DESCRIPTION OF VARIOUS EMBODIMENTS

The system described herein provides a mechanism for continuous non-contact identification of sleep and wake periods of a user along with sleeping positions and patterns of turning in bed based on classifiers acquired through machine learning and other algorithms and utilizing velocity, coordinate and directional data collected from point clouds, obtained by an always-on tracking device, embedded into a room or other facility where the user resides.

Figure 1:
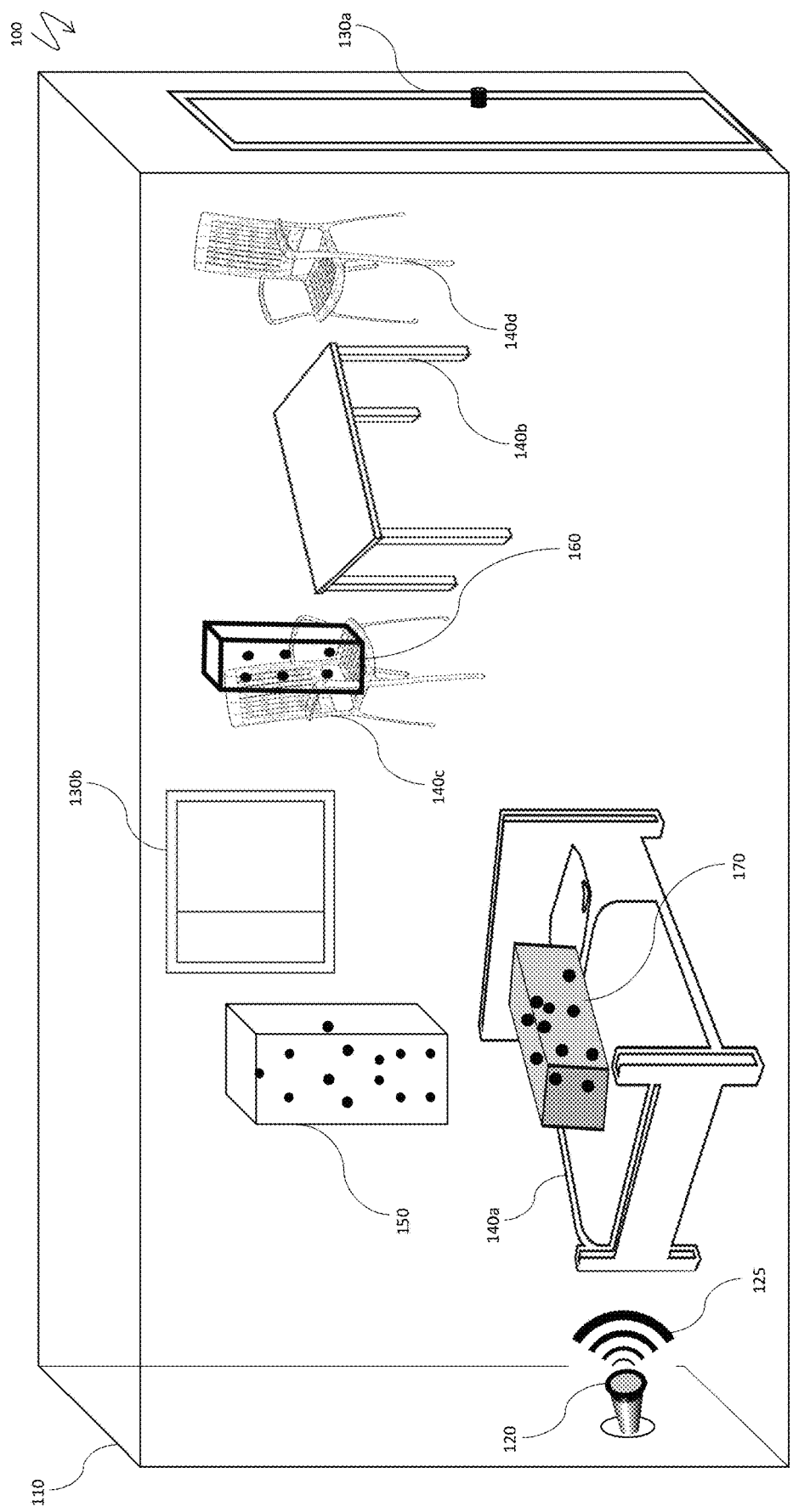
FIG. 1 is a schematic illustration of a room, furniture, non-contact tracking device and point clouds for various user states, according to an embodiment of the system described herein.

FIG. 1 is a schematic illustration 100 of a room 110, furniture, non-contact tracking device and point clouds for various user states. A user resides in the room 110 that has a tracking device 120 plugged into an AC outlet on a wall where a radar signal 125 is used to track object movement in the room. The room 110 has a door 130a, a window 130b and is furnished with a bed 140a, a table 140b, and a couple of chairs 140c, 140d. FIG. 1 illustrates a first point cloud 150 tracking the user walking to the window 130b. The first point cloud has a denser point cloud and a larger size bounding box compared with a second point cloud 160, corresponding to the user sitting on the chair 140c, and a third point cloud 170 showing the user lying on the bed 140a.

Figure 2:
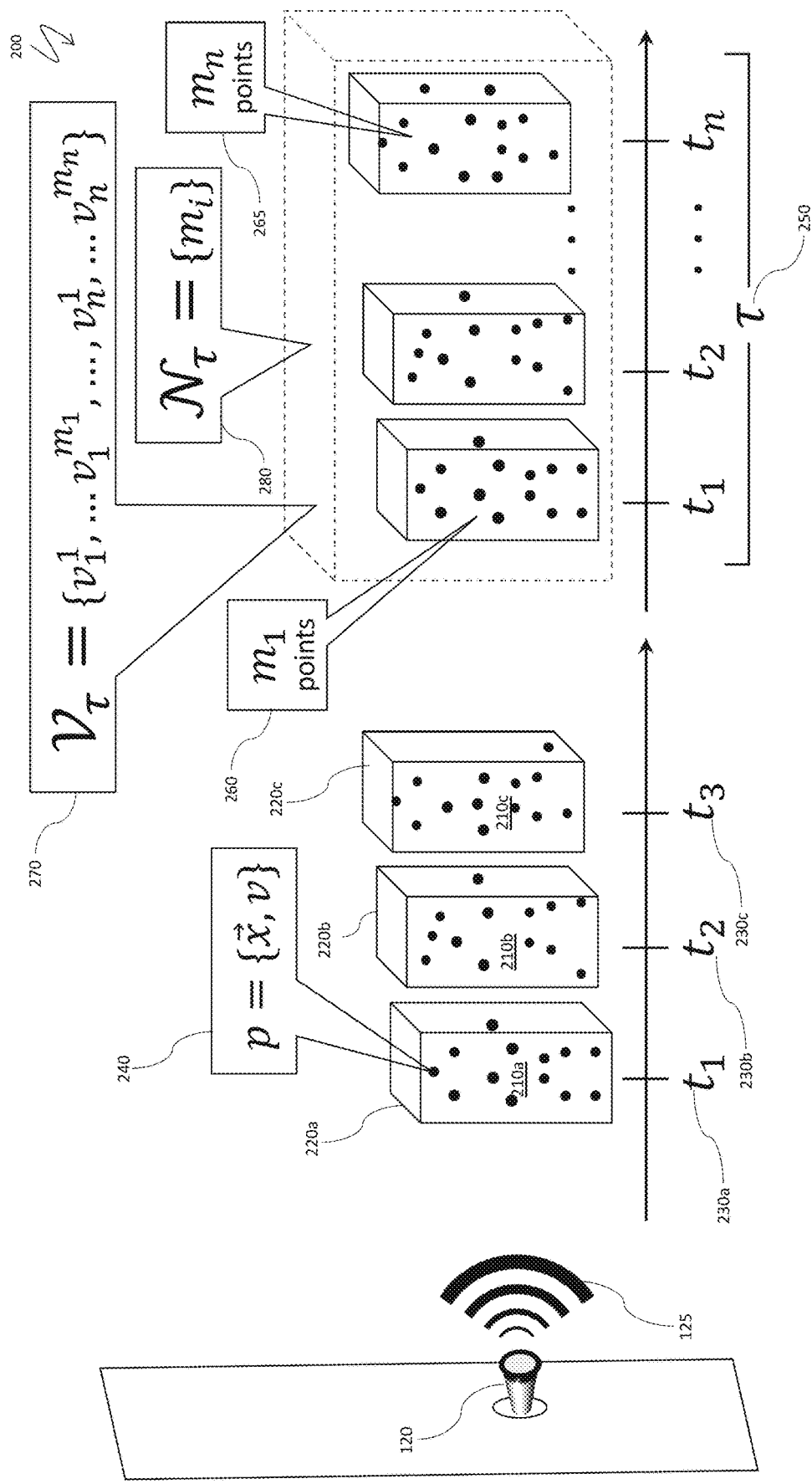
FIG. 2 is a schematic illustration of an intermediate data assembly from raw data for short-term feature extraction, according to an embodiment of the system described herein.

FIG. 2 is a schematic illustration 200 of intermediate data assembly from raw data for short-term feature extraction. The tracking device 120 emitting the radar signal 125 produces point clouds 210a-210c with bounding boxes 220a-220c for frames 230a-230c. Each point 240 of the point clouds 210a-210c may be characterized by coordinates and radial scalar velocity, p={$\vec{x}$, v} ($\vec{x}$ is a three-dimensional coordinate vector, V is a velocity having a sign that depends on a radial direction to/from the tracking device).

A time slot 250, $\tau=\{t_1, \ldots t_n\}$, includes n frames $t_i$ with $m_i$ points in the point cloud corresponding to the i-th frame, so that a first point cloud 260 has $m_1$ points and a last, n-th point cloud 265 has $m_n$ points. A bag of velocities 270 for the slot τ includes all point velocities for the point clouds in the slot, $\mathcal{V}_{\tau_\tau}=\{v_1^1, v_1^{m_1}, \ldots v_n^1, \ldots v_n^{m_n}\}$, while a bag of point counts 280 includes all point counts in the slot, $\mathcal{N}_{\tau_\tau}=\{m_1, \ldots m_n\}$.

Figure 3:
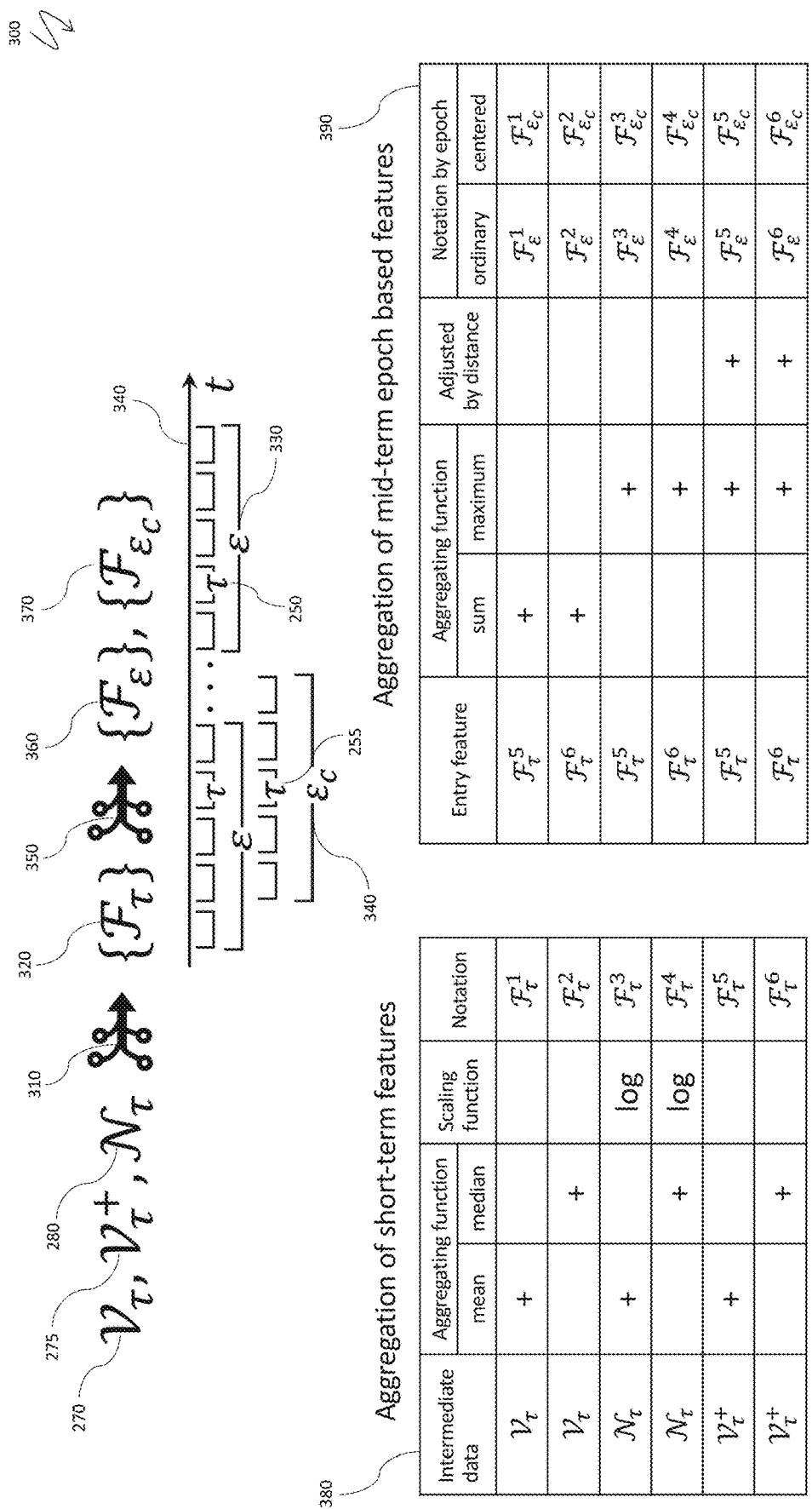
FIG. 3 is a schematic illustration of feature construction, according to an embodiment of the system described herein.

FIG. 3 is a schematic illustration 300 of feature construction for training purposes. Intermediate data, corresponding to a time slot T and captured by the tracking device, includes the bag of velocities 270 ($\mathcal{V}_{\tau_\tau}$), the bag of point counts 280 ($\mathcal{N}_{\tau_\tau}$) and a bag of absolute velocities 275 ($\mathcal{V}_{\tau_\tau}^+$), which are unsigned values corresponding to the bag of velocities 270 ($\mathcal{V}_{\tau_\tau}$), as explained elsewhere herein. One or multiple aggregating, scaling and filtering functions 310 may be applied to the intermediate data, resulting in a set of short-term (slot-related) features 320 ($\mathcal{F}_{\tau_\tau}$) used as a training set in machine learning. Subsequently, short-term features are aggregated into mid-term, epoch-related features as follows: (i) an ordinary epoch 330 (ε) combines several adjacent slots 250; ordinary epochs form a sequence of time intervals of equal lengths from a start of data collection session; (ii) a centered epoch 340 ($\varepsilon_c$) surrounding a particular slot 255 placed in a center of the slot 255, similarly to a configuration of sliding averages; (iii) another set of aggregating, scaling and filtering functions 350 is applied to all short-term features within an ordinary or a centered epoch to produce mid-term, epoch related features 360 ($\mathcal{F}_{\tau_\varepsilon}$), 370 ($\mathcal{F}_{\tau_{\varepsilon_c}}$). Mid-term features are also added to the training set.

Tables 380, 390 illustrate short-term and mid-term feature aggregation and are similar to Tables 1, 2, described above. In the table 380, the intermediate data $\mathcal{V}_{\tau_\tau}$, $\mathcal{N}_{\tau_\tau}$, $\mathcal{V}_{\tau_\tau}^+$ are aggregated into six short-term features $\mathcal{F}_{\tau_\tau}^1$–$\mathcal{F}_{\tau_\tau}^6$ using four aggregation and scaling functions: two of the functions use aggregation through mean and median values without scaling, while two other ones of the functions add logarithmic scaling. The table 390 illustrates aggregation of two short-term features from the table 380, $\mathcal{F}_{\tau_\tau}^5$ and $\mathcal{F}_{\tau_\tau}^6$, into twelve mid-term features, six for ordinary epochs and six for centered epochs, using four different aggregation and filtering functions: two of the filtering functions use aggregation through sum and maximum values without filtering, while two other ones of the filtering functions add filtering by distance from the tracking device 120 of FIG. 1, as explained elsewhere herein.

Figure 4:
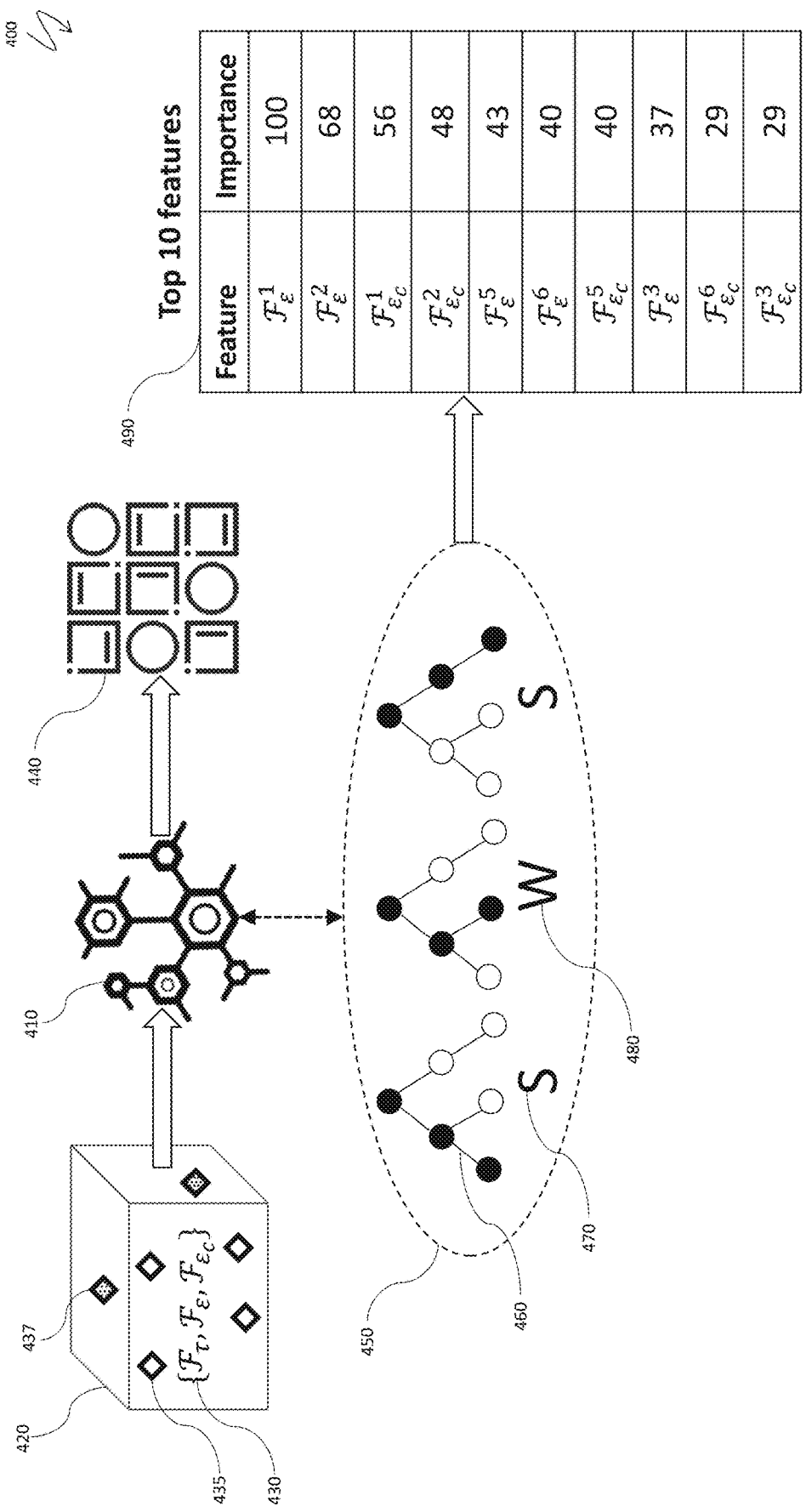
FIG. 4 is a schematic illustration of machine learning and feature ranking, according to an embodiment of the system described herein.

FIG. 4 is a schematic illustration 400 of machine learning and feature ranking. At a training phase, a machine learning module 410 processes a training set in a multi-dimensional feature space 420. The training set includes points 430, one point per slot τ; coordinates of each of the points 430 combine short-term features $\mathcal{F}_{\tau_\tau}$ for the slot τ, mid-term features $\mathcal{F}_{\tau_\varepsilon}$ for the only ordinary epoch E that contains the slot τ, and mid-term features $\mathcal{F}_{\tau_{\varepsilon_c}}$ for the only centered epoch $\varepsilon_c$ that has the slot τ as a center of the centered epoch $\varepsilon_c$ (see FIGS. 2, 3 and the accompanying texts for details). Each point of the training set corresponds to a sleep state 435 (illustrated with unfilled shapes) or a wake state 437 (filled shapes).

The machine learning module builds a sleep/wake state classifier 440. Machine learning may employ a random forest method 450, whereby decision trees 460, corresponding to sleep outcomes 470 and wake outcomes 480 are created for the classification purpose. The random forest method also allows for feature ranking, which is illustrated by a table 490, which includes a top ten most important features from the table 390 in FIG. 3 (the table 490 is similar to the Table 3, discussed above).

FIGS. 5A-5D are schematic illustrations of identifying sleeping positions of a user.

FIG. 5A illustrates identification of a sleeping position of the user when the user is lying on a bed 510 and is sleeping on the back of the user as shown by a pictogram 520. In this case, the chest of the user, represented by an upper face 560c of a bounding box of a point cloud, is moving up and down between an upper position 590i (full inhale) and a lower position 590e (full exhale), as shown by a vertical line 580ud. The vertical movement is captured by the tracking device 120. A heart area 570 of the user, also identified by the tracking device 120 that detects heart beats, is shifted to the left side of the body of the user, represented by a left face 560l of the bounding box. Accordingly, the combination of two features: the up-and-down oscillation illustrated by the vertical line 580ud of the bounding box of the point cloud and location of the heart area 570 closer to the left face 560l of the bounding box of the point cloud may serve as indicators of the sleeping position of FIG. 5A.

FIG. 5B illustrates identification of a sleeping position of the user on the stomach of the user as shown by a pictogram 530. In this case, the back of the user represented by an upper face 560b of a bounding box of a point cloud, is moving up and down as shown by the vertical line 580ud, as explained in conjunction with FIG. 5A, while the heart area 570 is shifted further from a right face 560r of the bounding box (which corresponds to the right side of the body of the user). So, the combination of up-and-down oscillation illustrated by the vertical line 580ud of the bounding box of the point cloud and location of the heart area 570 further from the right face 560r of the bounding box of the point cloud may serve as indicators of the sleeping position of FIG. 5B.

FIG. 5C illustrates identification of a sleeping position of a user on the right side as shown by a pictogram 540. In the sleeping position of FIG. 5C, the chest and back of the user move left-and-right, as shown by a horizontal line 580lr. Two extreme coordinates for a face 560b of a bounding box, corresponding to the back of the user, correspond to full inhale 595i and full exhale 595e. The heart area 570 is closer to an upper face 560l of a bounding box, corresponding to the left side of the body of the user. Therefore, the combination of the left-and-right oscillation illustrated by the horizontal line 580lr of the bounding box and the location of the heart area 570 closer to the upper side 560l of the bounding box may be indicators of the sleeping position of FIG. 5C.

FIG. 5D illustrates identification of a sleeping position of the user on the left side as shown by a pictogram 550. In the sleeping position of FIG. 5D, the chest and back of the user move left-and-right, as shown by the horizontal line 580/r and as explained in conjunction with FIG. 5C. The heart area 570 is shifted further from an upper face 560r of the bounding box corresponding to the right side of the body of the user. Thus, the combination of left-and-right oscillation illustrated by the horizontal line 580/r of the bounding box and the location of the heart area 570 further from the upper side 560r of the bounding box represent two indicators of sleeping position of FIG. 5D.

Figure 6:
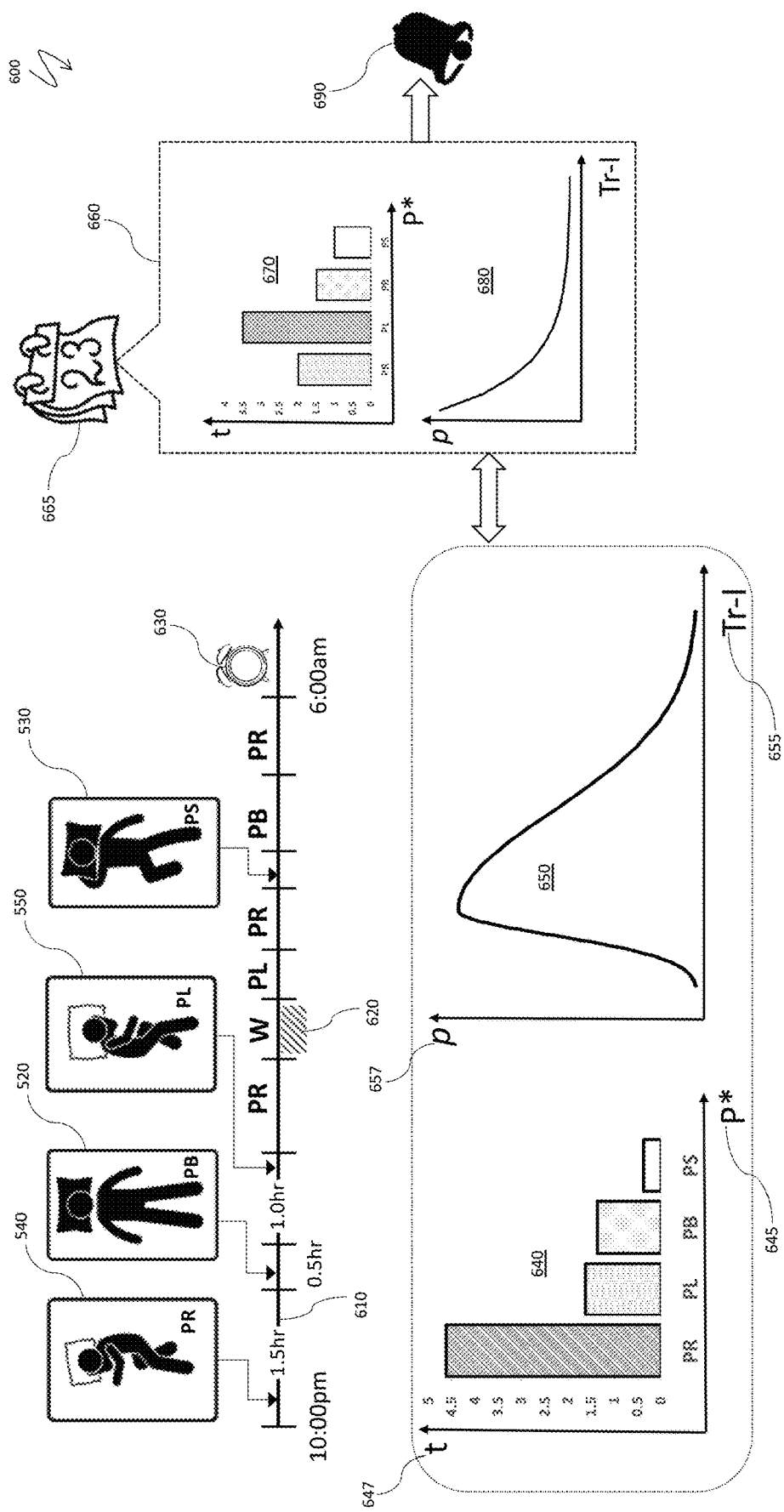
FIG. 6 is a schematic illustration of determining patterns of sleeping position and turning during sleep, according to an embodiment of the system described herein.

FIG. 6 is a schematic illustration 600 of determining patterns of sleeping position and turning during sleep. Intervals 610 of sleeping in each of the positions 540, 520, 550, 530, as well as wake intervals 620, may be recorded from a time the user goes to bed until a wake-up time 630. Based on data regarding sleep intervals and sleeping positions, collected through a sufficiently long period of time and processed statistically, the system may generate analytic representations of sleep patterns, such as a time distribution function 640 of sleeping positions 645 by average time 647 in each sleeping position and a probability distribution function 650 of sleeping intervals 655 between turning in bed by probability 657 thereof.

The system may subsequently track and process field data 660 corresponding to daily user behavior 665 and build analogous distribution functions 670, 680 for each daily sleep period. If the field distributions significantly deviate from long-term patterns 640, 650 (in the example in FIG. 6, both of the functions 670, 680 demonstrate dramatic difference from the patterns 640, 650), the system may generate an alarm 690 and alert care personnel about potential sleep problems encountered by the user.

Figure 7:
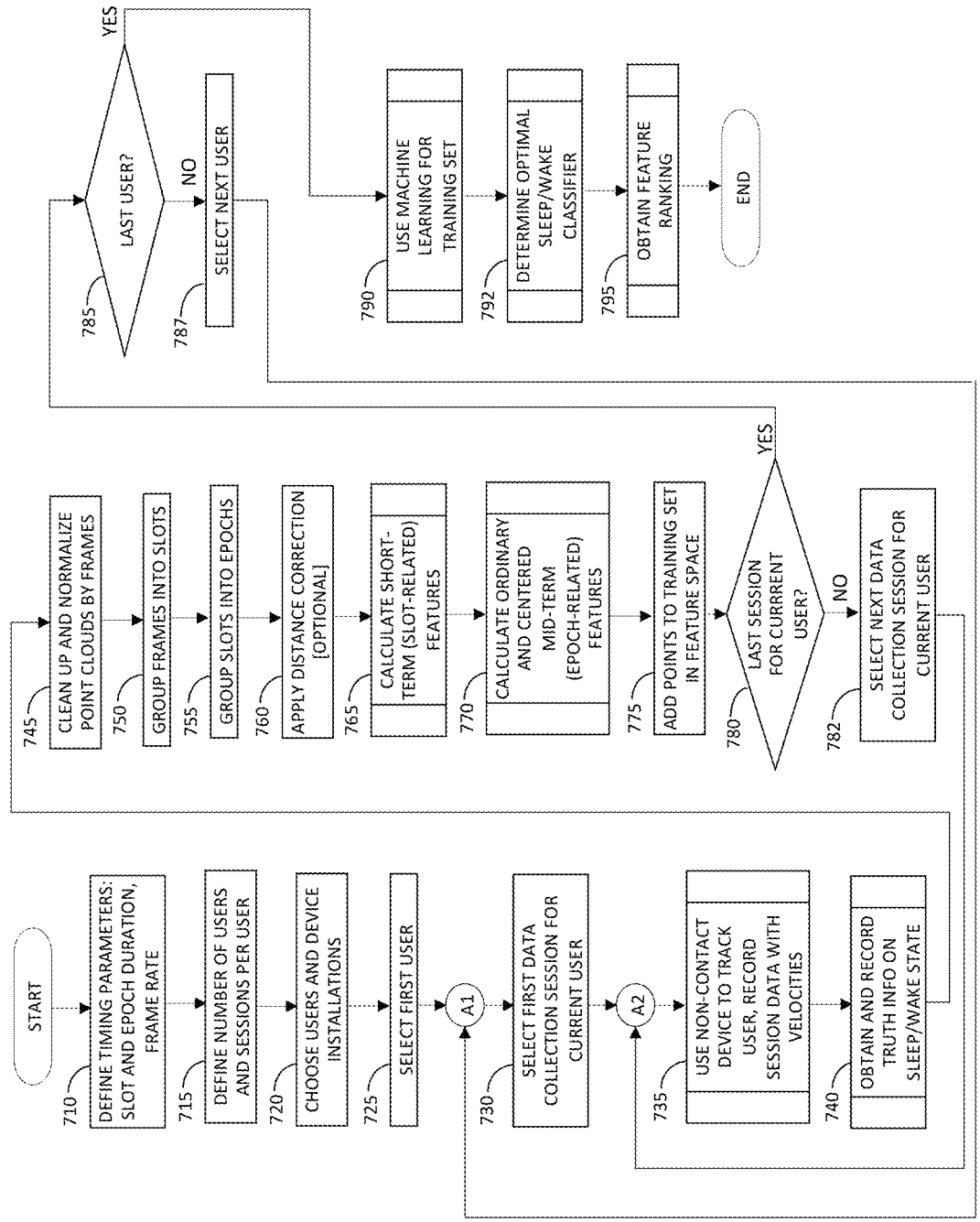
FIG. 7 is a system flow diagram illustrating system functioning in connection with sleep/wake classification, according to an embodiment of the system described herein.

Referring to FIG. 7, a system flow diagram 700 illustrates system functioning in connection with the sleep/wake classification. Processing begins at a step 710, where key timing parameters are defined, such as a frame rate per second, as well as slot and epoch duration. After the step 710, processing proceeds to a step 715, where number of users and number of sessions per user for collecting training data set are defined. After the step 715, processing proceeds to a step 720, where users are chosen and device installations are performed. After the step 720, processing proceeds to a step 725, where a first user is selected.

After the step 725, processing proceeds to a step 730, where a first data collection session for the current user is selected. After the step 730, processing proceeds to a step 735, where the system uses a non-contact device to track the user and record session data, including point velocities. After the step 735, processing proceeds to a step 740, where the system obtains and records truth info: the factual user sleep-wake state for each frame (for machine learning purpose), as explained elsewhere herein. After the step 740, processing proceeds to a step 745, where point clouds for various frames are cleaned up from noise and normalized. After the step 745, processing proceeds to a step 750, where frames are grouped into slots, as explained elsewhere herein (see, for example, FIG. 2 and the accompanying text). After the step 750, processing proceeds to a step 755, where slots are grouped into epochs (see, for instance, FIG. 3 and the accompanying text). After the step 755, processing proceeds to a step 760, where the system optionally applies distance related corrections or filtering, as explained elsewhere herein (see table 390 in FIG. 3 and the accompanying explanations). After the step 760, processing proceeds to a step 765, where the shot-term, slot-related features are calculated for all slots in the session. After the step 765, processing proceeds to a step 770, where ordinary and centered mid-term, epoch related features are calculated. After the step 770, processing proceeds to a step 775, where new points are added to the training data set in the feature space, as explained elsewhere herein (including FIG. 4 and the accompanying text).

After the step 775, processing proceeds to a test step 780, where it is determined whether the selected data collection session is the last session for the current user. If not, processing proceeds to a step 782, where the next data collection session for the current user is selected. After the step 782, processing proceeds back to the step 735, described above, which may be independently reached from the step 730. If it is determined at the test step 780 that the selected data collection session is the last session for the current user, processing proceeds to a test step 785, where it is determined whether the current user is the last user. If not, processing proceeds to a step 787, where the next user is selected. After the step 787, processing proceeds back to the step 730, described above, which may be independently reached from the step 725. If it is determined at the test step 785 that the current user is the last user, processing proceeds to a step 790, where the system uses machine learning for the accumulated training set. After the step 790, processing proceeds to a step 792, where an optimal sleep-wake classifier is determined as the result of machine learning. After the step 792, processing proceeds to a step 795, where feature ranking is obtained, as explained elsewhere herein (see, for example, FIG. 4 and the accompanying text). After the step 795, processing is complete.

Figure 8:
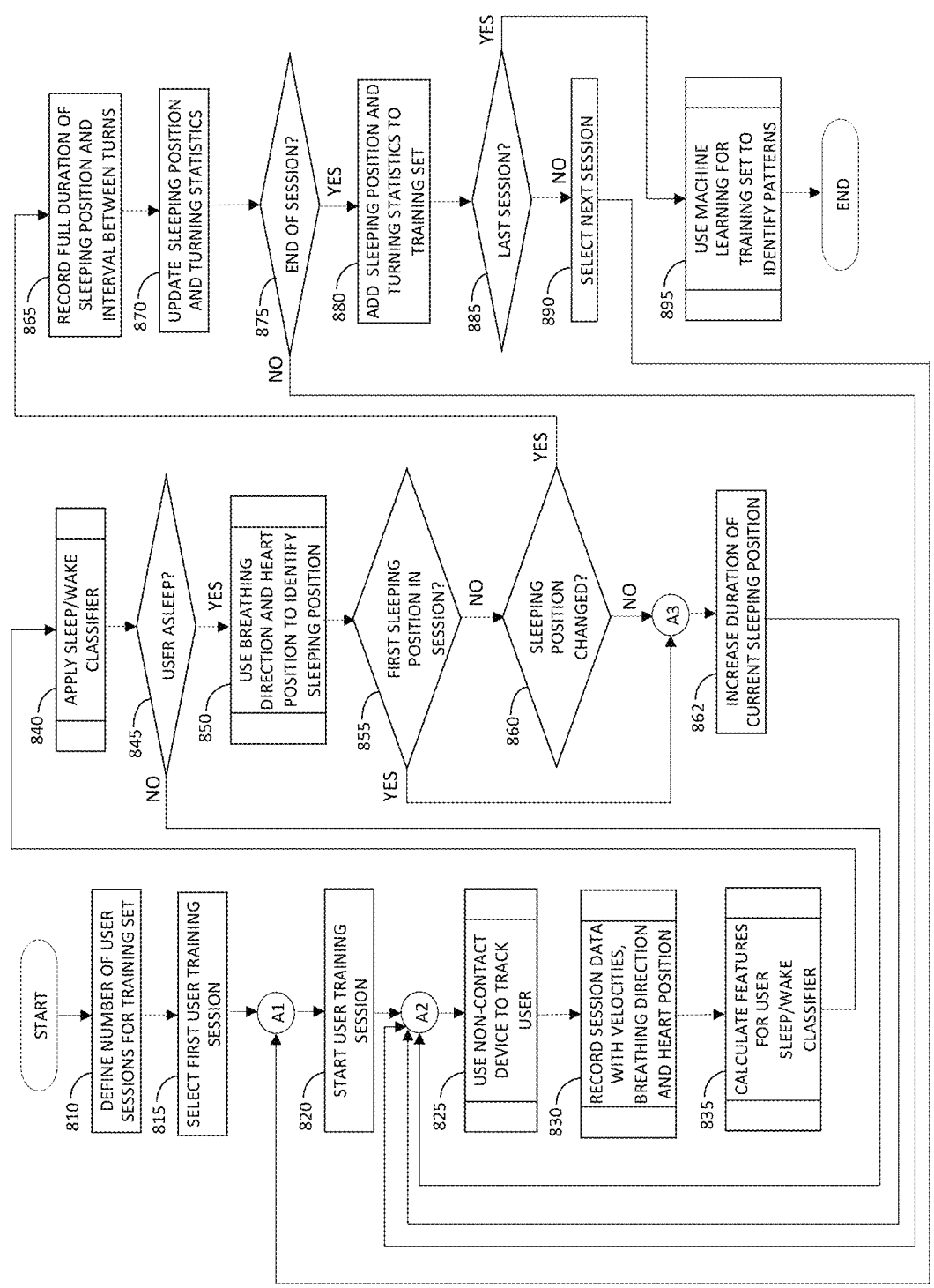
FIG. 8 is a system flow diagram illustrating system functioning in connection with identifying sleeping positions and turning patterns, according to an embodiment of the system described herein.

Referring to FIG. 8, a system flow diagram 800 illustrates system functioning in connection with identifying sleeping positions and turning patterns. Processing begins at a step 810, where the number of user sessions for a training set is determined. After the step 810, processing proceeds to a step 815, where a first training session for the user is selected. After the step 815, processing proceeds to a step 820, where the system starts a training session. After the step 820, processing proceeds to a step 825, where a non-contact tracking device monitors the user. After the step 825, processing proceeds to a step 830, where the system records session data (point clouds) with point velocities, breathing direction and heart position. After the step 830, processing proceeds to a step 835, where features are calculated for applying user sleep/wake classifier (see details, in particular, in conjunction with FIG. 7 and the accompanying text; this step in the flow diagram assumes that the sleep/wake classifier is already available).

After the step 835, processing proceeds to a step 840, where the system applies the sleep-wake classifier to features calculated at the step 835. After the step 840, processing proceeds to a test step 845, where it is determined whether the user is asleep. If not, processing proceeds to the step 825, described above, which may be independently reached from the step 820; otherwise, processing proceeds to a step 850, where a sleeping position of the user is identified utilizing breathing direction and location of the heart area, as explained elsewhere herein (see FIGS. 5A-5D and the accompanying text). After the step 850, processing proceeds to a test step 855, where it is determined whether the current sleeping position is the first captured sleeping position in the current training session. If so, processing proceeds to a step 862, where a duration of the current sleeping position is incrementally increased. After the step 862, processing proceeds back to the step 825, described above, which may be independently reached from the steps 820, 845.

If it is determined at the test step 855 that the identified sleeping position is not the first sleeping position during the current session, processing proceeds to a test step 860, where it is determined whether a sleeping position of the user has changed (i.e. the identified sleeping position is different from the previously registered sleeping position). If not, then processing proceeds to the step 862, described above, which may be independently reached from the step 855; otherwise, processing proceeds to a step 865, where the system records full duration of the previous sleeping position and interval between turns in the bed. After the step 865, processing proceeds to a step 870, where the system updates statistics of sleeping positions and intervals between turns. After the step 870, processing proceeds to a test step 875, where it is determined whether the current session has reached the end. If not, processing proceeds to the step 825, which may be independently reached from the steps 820, 845, 862; otherwise, processing proceeds to a step 880, where the statistics of sleeping positions and intervals between turns for the completed training session are added to the training set. After the step 880, processing proceeds to a test step 885, where it is determined whether the current session is the last session. If not, processing proceeds to a step 890 where the next session is selected. After the step 890, processing proceeds back to the step 820, described above, which may be independently reached from the step 815. If it is determined at the test step 885 that the current session is the last session, processing proceeds to a step 895 where the system uses machine learning for the constructed training set to identify patterns of sleeping position and turning in the bed. After the step 895, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Subsequently, system configurations and functions may vary from the illustrations presented herein. Further, various aspects of the system described herein may be implemented using various applications and may be deployed on various devices, including, but not limited to smartphones, tablets and other mobile computers. Smartphones and tablets may use operating system(s) selected from the group consisting of: iOS, Android OS, Windows Phone OS, Blackberry OS and mobile versions of Linux OS. Mobile computers and tablets may use operating system selected from the group consisting of Mac OS, Windows OS, Linux OS, Chrome OS.

Software implementations of the system described herein may include executable code that is stored in a computer readable medium and executed by one or more processors. The computer readable medium may be non-transitory and include a computer hard drive, ROM, RAM, flash memory, portable computer storage media such as a CD-ROM, a DVD-ROM, a flash drive, an SD card and/or other drive with, for example, a universal serial bus (USB) interface, and/or any other appropriate tangible or non-transitory computer readable medium or computer memory on which executable code may be stored and executed by a processor. The software may be bundled (pre-loaded), installed from an app store or downloaded from a location of a network operator. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of determining sleep patterns of a user, comprising:
   detecting a plurality of point clouds, each corresponding to a different position of the user at different times;
   forming a plurality of bounding boxes, each corresponding to coordinates of captured points of one of the point clouds;
   creating a wake/sleep classifier based on features of the point clouds;
   determining sleep positions of the user as a function of time based on the bounding boxes; and
   determining sleep patterns of the user based on the sleep positions of the user and on results of the sleep/wake classifier.

2. A method, according to claim 1, wherein detecting a plurality of point clouds includes using a tracking device to capture movements of the user.

3. A method, according to claim 2, wherein the tracking device uses radar.

4. A method, according to claim 1, wherein the features of the point clouds include intermediate data that is determined using at least one of: scalar velocities of points in the point clouds, absolute velocities of points in the point clouds, and counts of points in the point clouds.

5. A method, according to claim 4, wherein at least some of the features are filtered according to distance from a tracking device that is used to detect the plurality of point clouds.

6. A method, according to claim 5, wherein the intermediate data includes at least one of: a bag of point counts corresponding to a set of point counts at a series of sequential time frames, a bag of velocities corresponding to a set of point velocities at a series of sequential time frames, and a bag of absolute velocities corresponding to a set of absolute velocities at a series of sequential time frames.

7. A method, according to claim 6, wherein a set of aggregating, scaling and filtering functions are applied to the intermediate data to provide short-term feature aggregation values and mid-term feature aggregation values.

8. A method, according to claim 7, wherein the short-term feature aggregation values are determined based on time slots corresponding to a number of sequential time frames.

9. A method, according to claim 8, wherein the feature aggregation values include at least one of: mean values, median values, sum of values, minimum values and maximum values, and scaling function include logarithmic scaling function values.

10. A method, according to claim 8, wherein the mid-term feature aggregation values are derived from the short-term feature aggregation values.

11. A method, according to claim 10, wherein the mid-term feature aggregation values are determined based on epochs that represent contiguous collections of time slots.

12. A method, according to claim 1, wherein the features of the point clouds are used with truth information as training data for machine learning to provide an assessment of relative feature importance.

13. A method, according to claim 12, wherein the assessment of relative feature importance is determined using random forest machine learning.

14. A method, according to claim 1, wherein determining sleep positions includes determining if a breathing direction of the user is vertical or horizontal.

15. A method, according to claim 14, wherein, if the breathing direction is vertical, the sleep position is determined to be that the user is lying on the back of the user in response to a heart area of the user being detected on a left side of the user and the sleep position is determined to be that the user is lying on the stomach of the user in response to the heart area of the user being detected on a right side of the user.

16. A method, according to claim 14, wherein, if the breathing direction is horizontal, the sleep position is determined to be that the user is lying on a left of the user in response to a heart area of the user being detected in a relatively lower disposition and the sleep position is determined to be that the user is lying on a right side of the user in response to the heart area of the user being detected in a relatively upper disposition.

17. A method, according to claim 1, wherein sleep patterns of the user are determined based on correspondence of the sleep positions of the user with the results of the sleep/wake classifier as a function of time.

18. A method, according to claim 17, further comprising: tracking daily sleep patterns for the user.

19. A method, according to claim 18, further comprising: detecting a significant deviation from the daily sleep patterns.

20. A method, according to claim 19, further comprising: providing an alarm in response to detecting the significant deviation from the daily sleep patterns.

21. A non-transitory computer readable medium containing software that determines sleep patterns of a user, the software comprising:
executable code that detects a plurality of point clouds, each corresponding to a different position of the user at different times;
executable code that forms a plurality of bounding boxes, each corresponding to coordinates of captured points of one of the point clouds;
executable code that creates a wake/sleep classifier based on features of the point clouds;
executable code that determines sleep positions of the user as a function of time based on the bounding boxes; and
executable code that determines sleep patterns of the user based on the sleep positions of the user and on results of the sleep/wake classifier, wherein the features of the point clouds include intermediate data that is determined using at least one of: scalar velocities of points in the point clouds, absolute velocities of points in the point clouds, and counts of points in the point clouds.

22. A non-transitory computer readable medium containing software that determines sleep patterns of a user, the software comprising:
executable code that detects a plurality of point clouds, each corresponding to a different position of the user at different times;
executable code that forms a plurality of bounding boxes, each corresponding to coordinates of captured points of one of the point clouds;
executable code that creates a wake/sleep classifier based on features of the point clouds;
executable code that determines sleep positions of the user as a function of time based on the bounding boxes; and
executable code that determines sleep patterns of the user based on the sleep positions of the user and on results of the sleep/wake classifier, wherein determining sleep positions includes determining if a breathing direction of the user is vertical or horizontal.

\* \* \* \* \*